United States Patent [19]

Khan

[11] 4,002,609
[45] Jan. 11, 1977

[54] SUCROSE DERIVATIVES
[75] Inventor: Riaz Ahmed Khan, Sonning, England
[73] Assignee: Tate & Lyle Limited, London, England
[22] Filed: Feb. 24, 1975
[21] Appl. No.: 552,205
[30] Foreign Application Priority Data
Mar. 5, 1974 United Kingdom ............... 9867/74
[52] U.S. Cl. .............................................. 536/119
[51] Int. Cl.$^2$ ...................................... C08B 37/00
[58] Field of Search ................................ 260/234 R
[56] References Cited
UNITED STATES PATENTS
3,781,267   12/1973   Jaques et al. ................... 260/234 R OTHER PUBLICATIONS
Fieser et al., Reagents for Org. Syn., Wiley and Sons, 1967, pp. 1254–1255.

Primary Examiner—Lewis Gotts
Assistant Examiner—Cary Owens
Attorney, Agent, or Firm—Ostrolenk, Faber, Gerb & Soffen

[57] ABSTRACT

Two sucrose hepta-acetates, useful as synthetic intermediates in the preparation of functional sucrose derivatives, are obtained by tritylating sucrose, acetylating the resulting mixture of monotritylsucroses, and detritylating the resulting mixture of monotritylsucrose hepta-acetates. The previously known compound, 1',2,3,3',4,4',6-hepta-O-acetylsucrose, can be recovered by crystallization from the solution obtained in the detritylation step. When the remaining solution is subjected to retritylation and chromatography, it yields a new compound, 1',2,3,3',4',6,6'-hepta-O-acetylsucrose.

9 Claims, No Drawings

SUCROSE DERIVATIVES

This invention relates to sucrose derivatives. More particularly, the invention relates to sucrose derivatives having the formula:

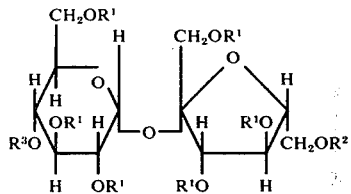

wherein:

$R^1 = R^3 = -COCH_3, R^2 = -H;$ (I)

or $R^1 = R^2 = -COCH_3, R^3 = -H.$ (II)

The compound of formula (I) is already known, while the compound of formula (II) is new.

The compound of formula (I), 1',2,3,3',4,4',6-hepta-O-acetylsucrose, is useful as an intermediate in the synthesis of 6'-substituted derivatives of sucrose, such as the halo- and deoxy-derivatives, sulphonates, azide, thiocyanate, thioacetate, amines, vinyl ethers and acryloyl esters. Various synthetic routes have been used for the preparation of this hepta-acetate, but they suffer from the disadvantage of being too complicated or giving very poor yields - i.e. under 20% and sometimes under 10%. The invention provides a new method for the synthesis of the known hepta-acetate of formula (I), which is capable of giving higher yields than the previously used methods and which also affords the new hepta-acetate of formula (II).

In accordance with the invention, the hepta-acetates of formulae (I) and (II) are prepared by a process which comprises: tritylating sucrose, to obtain a mixture of 6- and 60'-mono-O-tritylsucroses; acetylating the said mixture of monotritylsucroses, without first separating them from each other, to obtain a mixture of 6- and 6'-mono-O-tritylsucrose hepta-acetates; and detritylating the said mixture of monotritylsucrose hepta-acetates with hydrobromic acid in acetic acid solution.

Treatment of sucrose with triphenylchloromethane at about 0° C gives a mixture of 6- and 6'-mono-O-tritylsucroses. Without separating these two monotritylsucroses from each other, they are acetylated with acetic anhydride in pyridine, to obtain the corresponding monotritylsucrose hepta-acetates. Treatment of these monotritylsucrose hepta-acetates with hydrobromic acid in glacial acetic acid at about 0° C gives the sucrose hepta-acetates of formulae (I) and (II).

The known hepta-acetate of formula (I) can be recovered from the solution resulting from the detritylation step by crystallization. An overall yield of about 30% can be obtained, on the basis of the sucrose used in the tritylation step. It should be noted that, whereas the compound of formula (I) has previously been prepared via the monotrityl derivative, this has involved a tedious separation of 6'-mono-O-tritylsucrose from the 6-isomer by counter-current distribution; and it was therefore surprising to discover that a high yield of the hepta-acetate of formula (I) can be obtained simply by crystallization from the detritylation product when the two monotritylsucroses are not separated from each other, in accordance with the procedure of the present invention.

As well as providing a simplified procedure for the preparation of the hepta-acetate of formula (I), by avoiding the disadvantages of having to separate the two monotritylsucroses, the process of the present invention also affords the new hepta-acetate of formula (II). It is believed that this new compound forms during the detritylation of 6-mono-O-tritylsucrose hepta-acetate with hydrobromic acid, by the migration of an acetyl group from the carbon atoms at position 4 to that at position 6. In order to obtain the new hepta-acetate of formula (II), after crystallizing out the compound of formula (I), the solution resulting from the detritylation step is concentrated and retritylated by the same technique as used before. Sucrose hepta-acetates with free hydroxyl groups at the 6 and 6' positions undergo tritylation under these conditions; but the hepta-acetate of formula (II), with a free hydroxyl group at position 4, does not react. The sucrose hepta-acetate of formula (II) can then be separated from the 6- and 6'-mono-O-tritylsucrose hepta-acetates by chromatography.

The yield of the new sucrose hepta-acetate of formula (II) obtained by this procedure is relatively small, typically amounting to about 5%, on the basis of the sucrose used in the tritylation step. However, this yield can be improved by repeating the detritylation and retritylation steps one or more times, before the final separation by chromatography. During each detritylation step, more of the 6-mono-O-tritylsucrose hepta-acetate is converted to the sucrose hepta-acetate of formula (II), which does not react in the subsequent retritylation step. For example, it is found that when the solution remaining from the crystallization of the compound of formula (I) is subjected to retritylation, detritylation and a second retritylation, about 60% conversion to the hepta-acetate of formula (II) is obtained.

The hepta-acetate (II) is useful as an intermediate of 4-functional derivatives of sucrose, such as the keto-, halo- and deoxy-derivatives, the sulphonates, oximes, amines and azide, galactosucrose, and branched derivatives of sucrose.

The invention is illustrated by the following Example.

Example a. Mono-O-tritylation of sucrose

A solution of 100 g of sucrose in 1.5 liters of pyridine was treated with 80 g of triphenylchloromethane at 0° C. The reaction mixture was then kept at about 4° C for 14 days. The resulting solution was concentrated by codistillation with toluene, taken up in 1 liter of methylene chloride, washed with water and dried over sodium sulphate. The resulting solution was left to stand at room temperature, whereupon 28 g of a mixture of 6- and 6'-mono-O-tritylsucroses crystallized out. After filtering off this product, the filtrate was concentrated and eluted from a column of 1 kg of silica gel (Merck "Silica gel 60", 70-230 mesh ASTM), using a 1:1 by volume mixture of methylene chloride and acetone. The eluate was concentrated, giving a syrup from which a further 70 g of a mixture of 6- and 6'-mono-O- tritylsucroses was crystallized from acetone. Yield: 57.4%.

b. 1',2,3,3',4,4',6-Hepta-O-acetylsucrose (I)

A solution of 85 g of the mixture of mono-O-tritylsucroses obtained in part (a) above in 500 ml of pyridine was treated with 200 ml of acetic anhydride at room temperature for 24 hours. The resulting solution was concentrated by codistillation with toluene, giving 125 g of the corresponding hepta-acetates. Yield: 98.6%.
NMR (100 MHz):
  $\tau$ 4.17 (d, 1 proton, $J_{1,2}$ 3.5 Hz, H-1 due to 6-mono-O-tritylsucrose hepta-acetate); 4.3 (d, 1 proton, $J_{1,2}$ 3.5 Hz, H-1 due to 6'-mono-O-tritylsucrose hepta-acetate); 2.41 - 2.8 (m, protons due to trityl groups); 7.74 - 8.08 (m, protons due to acetates).

A solution of 110 g of the mono-O-tritylsucrose hepta-acetates thus obtained in a mixture of 160 ml of chloroform and 260 ml of glacial acetic acid was treated with 45 ml of 45% hydrobromic acid in glacial acetic acid at 0° C for 10 minutes. The tritanol formed was filtered off; and the filtrate was diluted with methylene chloride, washed successively with aqueous sodium sulphate, aqueous sodium hydrogen carbonate and water, and dried over sodium sulphate. The solution was then concentrated, and the remaining tritanol was removed from it by crystallization from methanol at 0° C. The resulting solution was concentrated to a syrup which, on crystallization from ether at 0° C, gave 42 g of the compound of formula (I). Yield: 52.9%.
m.p. and mixed m.p. = 158° – 160° C.
$[\alpha]_D^{20} = +54°$ ($c = 1.02$, chloroform).
NMR (100 MHz):
  $\tau$ 4.27 (d, 1 proton, $J_{1,2}$ 3.4 Hz, H-1);
  5.1 (q, 1 proton, $J_{2,3}$ 10.0 Hz, H-2);
  4.5 (t, 1 proton, $J_{3,4}$ 10.0 Hz, H-3);
  4.89 (t, 1 proton, $J_{4,5}$ 10.0 Hz, H-4);
  4.49 (d, 1 proton, $J_{3',4'}$ 6.0 Hz, H-3');
  7.25 (h, 1 proton, H-O);
  7.75 - 7.96 (m, 21 protons, Ac).

c. 1',2,3,3',4',6,6'-Hepta-O-acetylsucrose (II)

The filtrate obtained from the crystallization of the compound of formula (I) in part (b) above was concentrated to give 34.4 g of a syrup, which was treated with 30 g of triphenylchloromethane in 200 ml of pyridine at 70° – 75° C for 24 hours. The reaction mixture was diluted with methylene chloride, and washed successively with aqueous sodium hydrogen carbonate and water. The organic layer was separated off, dried over sodium sulphate, and concentrated by codistillation with toluene. The tritanol present was removed by crystallization from methanol, as in part (b) above. Thin layer chromatography of the resulting solution in a 7:1 by volume mixture of ether and petrol showed the presence of a fast-moving major component and a slow-moving minor component, which were coincident with 6- and 6'-mono-O-tritylsucrose hepta-acetates and the sucrose hepta-acetate (II), respectively. The solution was concentrated and chromatographed on a column of 500 g of silica gel (Merck "Silica gel 60", 70-230 mesh ASTM), eluted with a 5:1 by volume mixture of methylene chloride and petrol, giving first 26 g of a mixture of 6- and 6'-mono-O-tritylsucrose hepta-acetate, and then 4.5 g of the sucrose hepta-acetate of formula (II). Yield: 5.7%. $[\alpha]_D^{20} = +48.8°$ ($c = 1.16$, chloroform).
NMR (100 MHz):
  $\tau$ 4.36 (d, 1 proton, $J_{1,2}$ 3.5 Hz, H-1);
  5.7 (q, 1 proton, $J_{2,3}$ 10.5 Hz, H-2);
  4.58 (t, 1 proton, $J_{3,4}$ 10.5 Hz, H-3);
  4.5 (d, 1 proton, $J_{3',4'}$ 6.0 Hz, H-3+);
  4.63 (t, 1 proton, $J_{4',5'}$ 6.0 Hz. H-4');
  7.73 - 7.9 (m, 21 protons, 7 Ac).

The structure of the hepta-acetate of formula (II) was confirmed by treating 2 g of it with 2 ml of methanesulphonyl chloride in 50 ml of pyridine, initially at 0° C and then with stirring at room temperature for 24 hours, which gave 2 g of 4-O-methanesulphonylsucrose hepta-acetate.
Yield: 88%.
m.p. and mixed m.p. = 94° - 95° C.

The IR and NMR spectra of the 4-O-methanesulphonylsucrose hepta-acetate thus obtained were identical with those of a standard sample.

I claim:

1. A process for preparing 1',2,3,3',4,4',6-hepta-O-acetylsucrose and 1',2,3,3',4',6,6'-hepta-O-acetylsucrose, which comprises the successive steps of: tritylating sucrose, whereby there is obtained a mixture of 6- and 6'-mono-O-tritylsucroses; acetylating said mixture of monotritylsucroses, without first separating them from each other, whereby there is obtained a mixture of 6- and 6'-mono-O-tritylsucrose hepta-acetates; and detritylating said mixture of monotritylsucrose hepta-acetates with hydrobromic acid in acetic acid solution.

2. A process for preparing 1',2,3,3',4,4',6-hepta-O-acetylsucrose, which comprises the successive steps of tritylating sucrose, whereby there is obtained a mixture of 6- and 6'-mono-O-tritylsucroses; acetylating said mixture of monotritylsucroses, without first separating them from each other, whereby there is obtained a mixture of 6- and 6'-mono-O-tritylsucrose hepta-acetates; detritylating said mixture of monotritylsucrose hepta-acetates with hydrobromic acid in acetic acid solution, whereby there is obtained a mixture of sucrose hepta-acetates; and recovering 1',2,3,3',4,4',6-hepta-O-acetylsucrose by crystallization from said mixture of sucrose hepta-acetates.

3. A process for preparing 1',2,3,3',4',6,6'-hepta-O-acetylsucrose, which comprises the successive steps of: tritylating sucrose, whereby there is obtained a mixture of 6- and 6'-mono-O-tritylsucroses; acetylating said mixture of monotritylsucroses, without first separating them from each other, whereby there is obtained a mixture of 6- and 6'-mono-O-tritylsucrose hepta-acetates; detritylating said mixture of monotritylsucrose hepta-acetates with hydrobromic acid in acetic acid solution, whereby there is obtained a mixture of sucrose hepta-acetates; recovering 1',2,3,3',4,4',6-hepta-O-acetylsucrose by crystallization from said mixture of sucrose hepta-acetates; retritylating the solution remaining after said crystallization; and recovering 1',2,3,3',4',6,6'-hepta-O-acetylsucrose by subjecting the product of the retritylation step to chromotography.

4. A process according to claim 3, wherein said product of the retritylation step is subjected at least once to the successive steps of detritylation and further retritylation before being subjected to chromotography.

5. 1',2,3,3',4',6,6'-Hepta-O-acetylsucrose.

6. A process according to claim 1 wherein said tritylating is effected by reacting said sucrose with triphenylchloromethane and wherein said acetylating is effected by reacting said mixture with acetic anhydride.

7. A process according to claim 2 wherein said tritylating is effected by reacting said sucrose with triphenylchloromethane and wherein said acetylating is effected by reacting said mixture with acetic anhydride.

8. A process according to claim 3 wherein said tritylating is effected by reacting said sucrose with triphenylchloromethane and wherein said acetylating is effected by reacting said mixture with acetic anhydride.

9. A process according to claim 4 wherein said tritylating is effected by reacting said sucrose with triphenylchloromethane and wherein said acetylating is effected by reacting said mixture with acetic anhydride.

* * * * *